(12) United States Patent
Zanker

(10) Patent No.: US 6,769,293 B2
(45) Date of Patent: Aug. 3, 2004

(54) DETECTION OF LIQUID IN GAS PIPELINE (75) Inventor: Klaus Joachim Zanker, Houston, TX (US)

(73) Assignee: Daniel Industries, Inc., Houston, TX (US)

(*) Notice: Subject to any disclaimer, the term of this patent is extended or adjusted under 35 U.S.C. 154(b) by 90 days.

(21) Appl. No.: 10/037,936

(22) Filed: Jan. 4, 2002

(65) Prior Publication Data
US 2002/0078737 A1 Jun. 27, 2002

Related U.S. Application Data (63) Continuation-in-part of application No. 09/388,253, filed on Sep. 1, 1999, now Pat. No. 6,386,018.

(51) Int. Cl.$^7$ .................. G01N 29/02; G01N 29/18; G01N 29/26

(52) U.S. Cl. .............. 73/61.79; 73/861.04; 73/149; 73/597

(58) Field of Search ................ 73/61.79, 149, 73/290 V, 597, 861.04

(56) References Cited

U.S. PATENT DOCUMENTS

| | | | |
|---|---|---|---|
| 3,623,363 A | * 11/1971 | Dory | .......... 73/61.45 |
| 4,646,575 A | * 3/1987 | O'Hair et al. | ........... 73/861.31 |
| 5,616,856 A | * 4/1997 | Castel | .......... 73/61.45 |
| 5,719,329 A | * 2/1998 | Jepson et al. | .............. 73/61.49 |

* cited by examiner

Primary Examiner—Daniel S. Larkin
(74) Attorney, Agent, or Firm—Conley Rose, P.C.

(57) ABSTRACT

An apparatus and related method for measuring the presence or degree of stratified flow in a two-phase flow is disclosed. A first speed of sound for the fluid flowing through the pipeline is measured for an ultrasonic signal that would reflect from stratified flow, if present. A second speed of sound is measured at a location that would not reflect off the stratified flow. A difference in these two measurements indicates the presence of stratified flow. The level of stratified flow can be determined based on the magnitude of the difference.

25 Claims, 7 Drawing Sheets

DETECTION OF LIQUID IN GAS PIPELINE

CROSS-REFERENCE TO RELATED APPLICATIONS

This application is a continuation-in-part and claims benefit to pending U.S. patent application Ser. No. 09/388,253 filed Sep. 1, 1999 now U.S. Pat. No. 6,386,018 entitled "Ultrasonic two-Phase Flow Apparatus and Stratified Level Detector."

STATEMENT REGARDING FEDERALLY SPONSORED RESEARCH OR DEVELOPMENT

Not Applicable.

BACKGROUND OF THE INVENTION

1. Field of the Invention

The invention relates generally to the detection of liquid in a pipeline. More particularly, embodiments of the invention relate to the detection of stratified flow in a pipeline. An embodiment of the invention detects the presence and volume of stratified flow in a pipeline based on time of flight or velocity of sound measurements for an ultrasonic meter.

2. Description of the Related Art

After a hydrocarbon, such as natural gas, has been removed from the ground, it is commonly transported from place to place via pipelines. Often this gas stream also contains a certain amount, or percent fraction, of liquid. As is appreciated by those of skill in the art, it is desirable to know with accuracy the amount of gas in the gas stream. It is also extremely desirable to know whether liquid is being transported along with the gas stream. For example, the presence of a stratified flow of liquid in the gas stream may indicate a production problem upstream of the measurement device. A "stratified flow" of liquid consists of a stream or river traveling along one area of the pipeline, such as the bottom. If the measurement device is at the location where the gas is changing hands or custody, and if the gas contains "natural gas liquids" or condensates, a seller of gas wants extra compensation for this energy-rich liquid.

Gas flow meters have been developed to determine how much gas is flowing through the pipeline. One type of meter to measure gas flow is called an ultrasonic flow meter. Ultrasonic flow meters are also named sonic or acoustic flow meters.

Figure 1A:
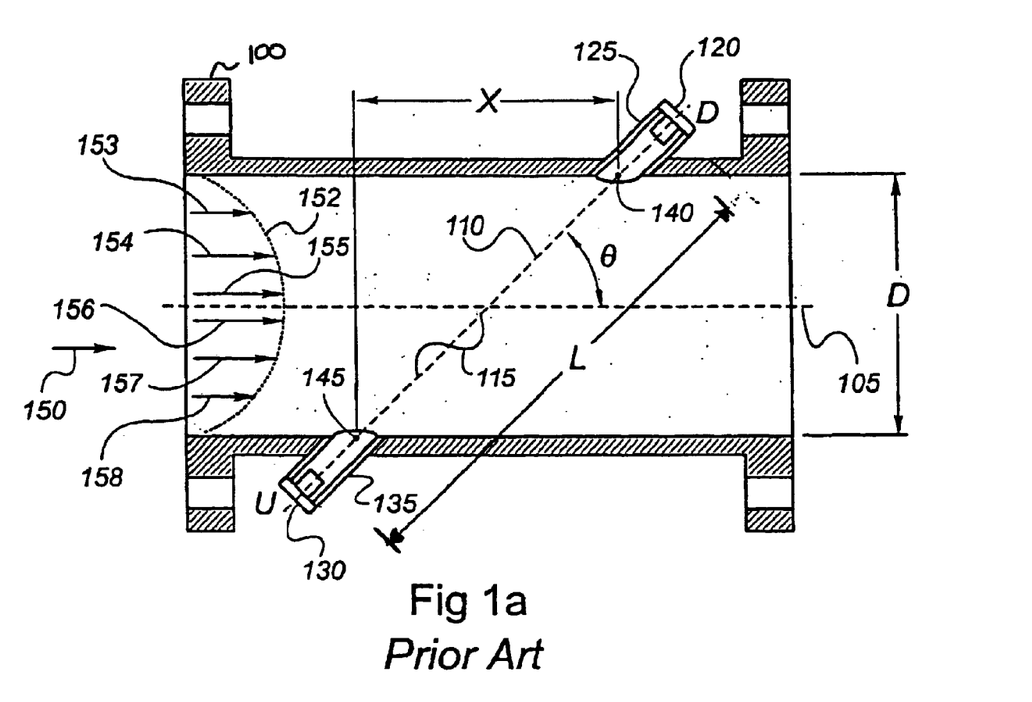
FIG. 1A is a cut-away top view of an ultrasonic gas flow meter.

FIG. 1A shows an ultrasonic meter suitable for measuring gas flow. Spoolpiece 100, suitable for placement between sections of gas pipeline, has a predetermined size and thus defines a measurement section. A pair of transducers 120 and 130, and their respective housings 125 and 135, are located along the length of spoolpiece 100. A path 110, sometimes referred to as a "chord" exists between transducers 120 and 130 at an angle θ to a centerline 105. The position of transducers 120 and 130 may be defined by this angle, or may be defined by a first length L measured between transducers 120 and 130, a second length X corresponding to the axial distance between points 140 and 145, and a third length D corresponding to the pipe diameter. Distances X, D and L are precisely determined during meter fabrication. Points 140 and 145 define the locations where acoustic signals generated by transducers 120 and 130 enter and leave gas flowing through the spoolpiece 100 (i.e. the entrance to the spoolpiece bore). In most instances, meter transducers, such as 120 and 130, are placed a specific distance from points 140 and 145, respectively, regardless of meter size (i.e. spoolpiece size). A fluid, typically natural gas, flows in a direction 150 with a velocity profile 152. Velocity vectors 153–158 indicate that the gas velocity through spool piece 100 increases as centerline 105 of spoolpiece 100 is approached.

Transducers 120 and 130 are ultrasonic transceivers, meaning that they both generate and receive ultrasonic signals. "Ultrasonic" in this context refers to frequencies above about 20 kilohertz. Typically, these signals are generated and received by a piezoelectric element in each transducer. Initially, D (downstream) transducer 120 generates an ultrasonic signal that is then received at, and detected by, U (upstream) transducer 130. Some time later, U transducer 130 generates a reciprocal ultrasonic signal that is subsequently received at and detected by D transducer 120. Thus, U and D transducers 130 and 120 play "pitch and catch" with ultrasonic signals 115 along chordal path 110. During operation, this sequence may occur thousands of times per minute.

The transit time of the ultrasonic wave 115 between transducers U 130 and D 120 depends in part upon whether the ultrasonic signal 115 is traveling upstream or downstream with respect to the flowing gas. The transit time for an ultrasonic signal traveling downstream (i.e. in the same direction as the flow) is less than its transit time when traveling upstream (i.e. against the flow). The upstream and downstream transit times can be used to calculate the average velocity along the signal path. In particular, the transit time $t_1$, of an ultrasonic signal traveling against the fluid flow and the transit time $t_2$ of an ultrasonic signal travelling with the fluid flow may be defined:

$$t_1 = \frac{L}{c - V\frac{x}{L}} \quad (1)$$

$$t_2 = \frac{L}{c + V\frac{x}{L}} \quad (2)$$

where,
c=speed of sound in the fluid flow;
V=average axial velocity of the fluid flow over the chordal path in the axial direction;
L=acoustic path length;
x=axial component of L within the meter bore;
$t_1$=transmit time of the ultrasonic signal against the fluid flow; and
$t_2$=transit time of the ultrasonic signal with the fluid flow.

The upstream and downstream transit times can be used to calculate the average velocity along the signal path by the equation:

$$V = \frac{L^2}{2x} \frac{t_2}{t_1 t_2} \quad (3)$$

with the variables being defined as above.

The upstream and downstream travel times may also be used to calculate the speed of sound in the fluid flow according to the equation:

$$c = \frac{L}{2} t_1 + \frac{t_2}{t_1 t_2} \quad (4)$$

Given the cross-section measurements of the meter carrying the gas, the average velocity over the area of the gas may be used to find the quantity of gas flowing through spoolpiece 100. Typically, these measurements are based on a batch of ten to thirty ultrasonic signals rather than upon only one upstream and downstream signal. Alternately, a meter may be designed to attach to a pipeline section by, for example, hot tapping, so that the pipeline dimensions instead of spoolpiece dimensions are used to determine the average velocity of the flowing gas.

In addition, ultrasonic gas flow meters can have one or more paths. Single-path meters typically include a pair of transducers that projects ultrasonic waves over a single path across the axis (i.e. center) of spoolpiece 100. In addition to the advantages provided by single-path ultrasonic meters, ultrasonic meters having more than one path have other advantages. These advantages make multi-path ultrasonic meters desirable for custody transfer applications where accuracy and reliability are crucial.

Figure 1B:
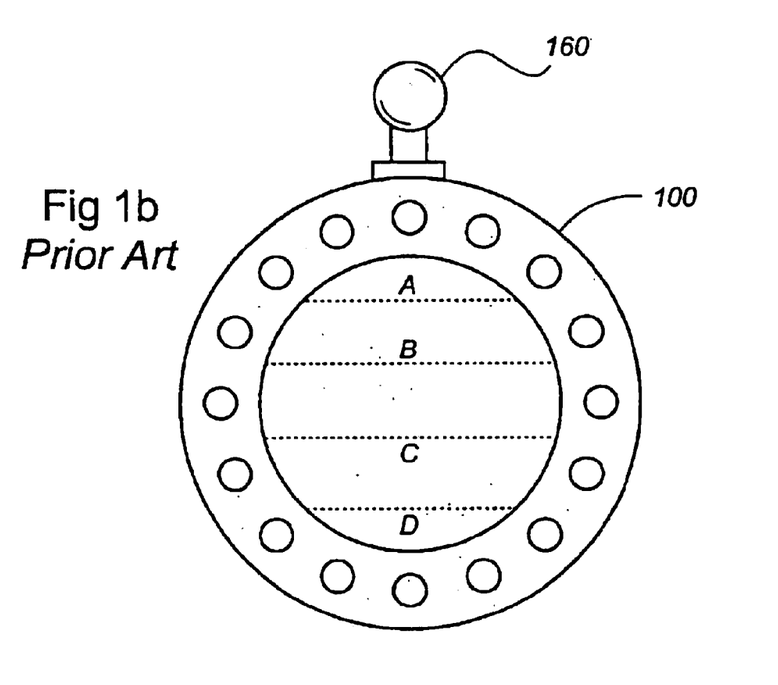
FIG. 1B is an end view of a spoolpiece including chordal paths A–D.

Referring now to FIG. 1B, a multi-path ultrasonic meter is shown. Spool piece 100 includes four chordal paths A, B, C, and D at varying levels through the gas flow. Each chordal path A–D corresponds to two transceivers behaving alternately as transmitter and receiver. Also shown is an electronics module 160, which acquires and processes the data from the four chordal paths A–D. This arrangement is described in U.S. Pat. No. 4,646,575, the teachings of which are hereby incorporated by reference. Hidden from view in FIG. 1B are the four pairs of transducers that correspond to chordal paths A–D.

Figure 1C:
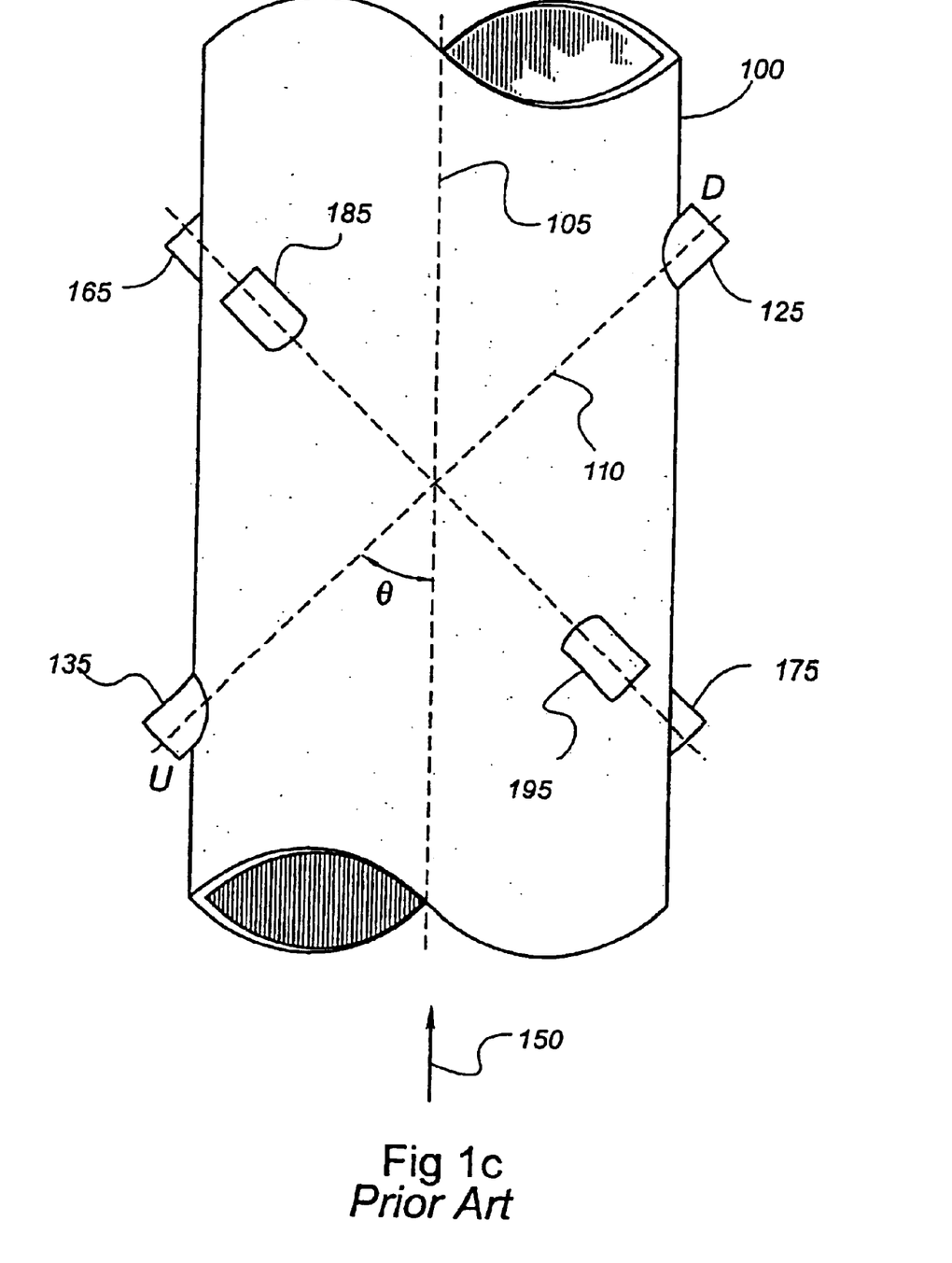
FIG. 1C is a top view of a spoolpiece housing transducer pairs.

The precise arrangement of the four pairs of transducers may be more easily understood by reference to FIG. 1C. Four pairs of transducer ports are mounted on spool piece 100. Each of these pairs of transducer ports corresponds to a single chordal path of FIG. 1B. A first pair of transducer ports 125 and 135 including transducers 120 and 130 is mounted at a non-perpendicular angle θ to centerline 105 of spool piece 100. Another pair of transducer ports 165 and 175 including associated transducers is mounted so that its chordal path loosely forms an "X" with respect to the chordal path of transducer ports 125 and 135. Similarly, transducer ports 185 and 195 are placed parallel to transducer ports 165 and 175 but at a different "level" (i.e. a different radial position in the pipe or meter spoolpiece). Not explicitly shown in FIG. 1C is a fourth pair of transducers and transducer ports. Taking FIGS. 1B and 1C together, the pairs of transducers are arranged such that the upper two pairs of transducers corresponding to chords A and B form an X and the lower two pairs of transducers corresponding to chords C and D also form an X.

Referring now to FIG. 1B, the flow velocity of the gas may be determined at each chord A-D to obtain chordal flow velocities. To obtain an average flow velocity over the entire pipe, the chordal flow velocities are multiplied by a set of predetermined constants. Such constants are well known and were determined theoretically.

This four-path configuration has been found to be highly accurate and cost effective. Nonetheless, other ultrasonic meter designs are known. For example, other ultrasonic meters employ reflective chordal paths, also known as "bounce" paths.

A pipeline may carry liquid in addition to the gas stream. Liquid level detectors are known that detect whether liquid is present at a location of interest, although typically these liquid level detectors are not positioned inside a pipeline.

One known design of ultrasonic meter is disclosed in U.S. Pat. No. 5,719,329 to Jepson. In particular, this patent discloses a multiphase flow meter that measures film heights of the fluids flowing though the meter by a very complicated scheme using the densities of the mediums in the meter, the pressure of the transmitted wave to the incident wave, and the velocity of sound in the medium. Unfortunately, this multiphase meter is likely too complicated for use in real world applications. The disclosure of the patent also includes a method to confirm the calculated film height by reflection of an ultrasonic signal from, and back to, a single transducer located on the bottom of the meter bore. Unfortunately, however, this method to determine film level is not very accurate (which may be why it is used only as a confirmation and not by itself).

Therefore, a meter or device is needed that is capable of detecting liquid in a pipeline. This device might also measure the amount of stratified flow in a gas stream. The device would be both simple and accurate enough to be used in real-world applications.

SUMMARY OF THE INVENTION

Disclosed embodiments of the invention include a method to determine the level of stratified flow in a conduit such as a pipeline, including transmitting an ultrasonic signal through a medium from a first transducer, reflecting the ultrasonic signal from the surface of the stratified flow, receiving the ultrasonic signal at a second transducer, and computing the speed of sound for the ultrasonic signal through the medium (the speed of sound may also be based on a batch of measurements along this same chord). A second speed of sound is also computed based on other ultrasonic signals. A difference in these two computed speeds of sound indicates the presence of stratified flow. Analysis of the difference in these two speeds of sound indicates the level of stratified flow in the pipeline.

The present invention comprises a combination of features and advantages that enable it to overcome various problems of prior devices. The various characteristics described above, as well as other features, will be readily apparent to those skilled in the art upon reading the following detailed description of the preferred embodiments of the invention, and by referring to the accompanying drawings.

BRIEF DESCRIPTION OF THE DRAWINGS

For a more detailed description of the preferred embodiment of the present invention, reference will now be made to the accompanying drawings, wherein.

DETAILED DESCRIPTION OF THE PREFERRED EMBODIMENT

Figure 2:
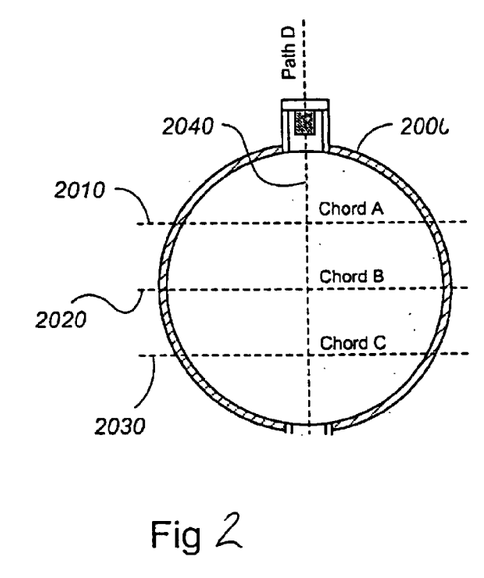
FIG. 2 is an end view of a multi-transducer level detector/ultrasonic flow meter combination.

FIG. 2 includes the end-view of a pipeline or spoolpiece 2000 for a multiple transducer level detector. As used herein, the term pipeline shall refer to either an actual pipeline or to a spoolpiece. Three chords 2010, 2020, 2030 (corresponding to a multi-path ultrasonic meter) are shown and are labeled as chords A, B, and C. Path D, labeled 2040, is also shown and corresponds to an additional, vertical chord. Of course, path D includes an upstream transducer and a downstream transducer. The transducers corresponding to path D may be positioned somewhere other than true vertical, so long as the length of path D changes with changes in stratified fluid. Chord D therefore may be the fourth chord of a four-chord ultrasonic meter, or may be used separately but in conjunction with an ultrasonic flow meter (or other device to measure the speed of sound in the gas) to establish the amount of stratified flow. Use of a four-chord ultrasonic meter is exemplary only and the disclosed multiple transducer level detector could be used with or be part of any multiple chord ultrasonic meter, including a meter having bounce paths. Nonetheless, use of a three horizontal chord design in conjunction with the disclosed level detector (or integrating the design into a four-chord meter) has certain advantages over the use of a traditional four horizontal-chord design. For example, the lowest chord on the four chordal path meter is easily flooded in stratified flow. An ultrasonic meter having three horizontal chords does not have this lowest chord, and thus avoids this problem. As already stated, the ultrasonic transducers corresponding to path D can be either separate from, or as a part of, such an ultrasonic meter. For these purposes, a level detector and an ultrasonic meter are thought of as two different devices that operate together to achieve a synergistic effect, but in actuality these two devices may equally be part of the same device and share components such as electronics, etc.

Figure 3:
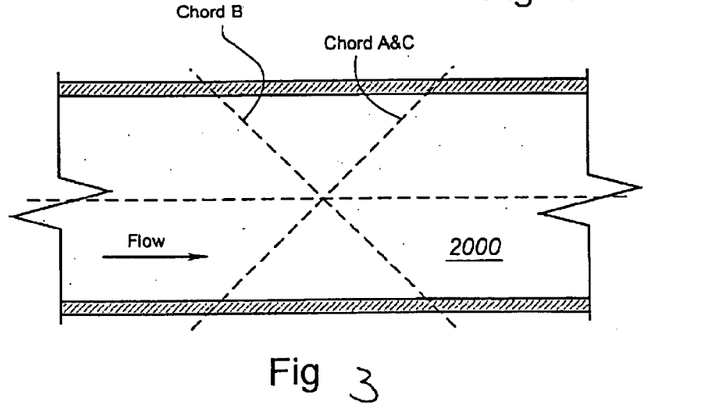
FIG. 3 is a top view of a pipeline showing flight paths for chords A, B, and C.
Figure 4:
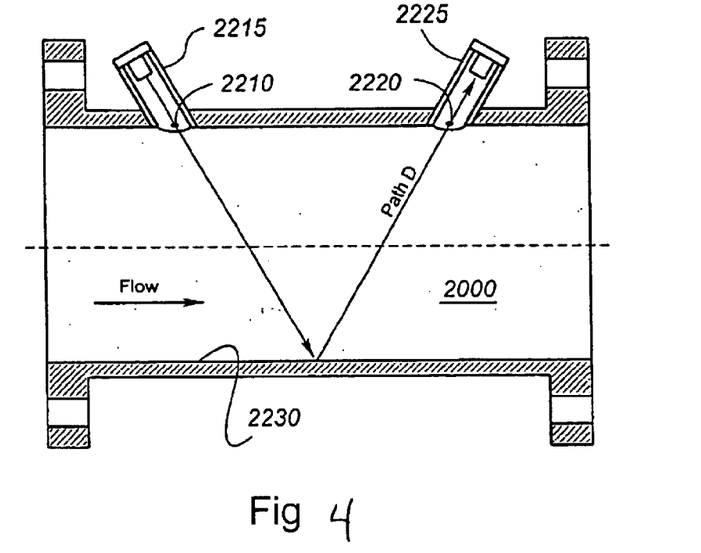
FIG. 4 is a side view of path D in a pipeline with no stratified flow.

FIG. 3 shows the pipeline 2000 from a top perspective and identifies a direction of flow, as well as chords A, B, and C. FIG. 4 includes a side view of pipeline 2000 when the pipeline does not contain a stratified two-phase flow. Path D originates at point 2210 corresponding to an ultrasonic transducer 2215, reflects off of the bottom 2230 of pipeline 2000 and travels to point 2220 corresponding to ultrasonic transducer 2225. The transducers 2215 and 2225 are preferably angled at about sixty degrees, although this is not a requirement of the invention. During operation transducers 2215 and 2225 preferably each generate ultrasonic signals that travel along path D and are detected by the other transducer, resulting in both an upstream and a downstream measurement. The measurement of both the upstream and downstream times of flight yields a speed of sound measurement for chord D.

Figure 5:
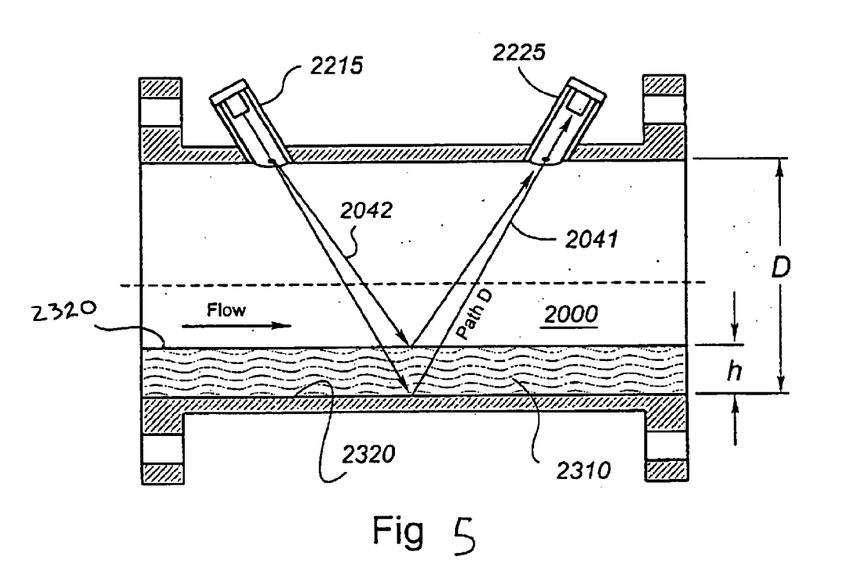
FIG. 5 is a side view of a pipeline having stratified flow contrasting the flight paths of path D.

FIG. 5 shows a side view of a pipeline 2000 containing a stratified flow 2310 of depth "h". In a pipeline, the area of the pipeline occupied by stratified flow will typically not exceed 10%. Pipeline 2000 includes ultrasonic transducers 2215 and 2225 that generate ultrasonic signals that travel along a first path D 2041. First path D 2041 corresponds to a pipeline without stratified flow as shown in FIG. 4. Second path D 2042, corresponding to a pipeline with a stratified flow, also is shown. Second path D 2042 corresponds to an ultrasonic signal that reflects off the surface 2320 of stratified flow 2310. In addition, it can be seen that second path D 2042 is slightly shorter than first path D 2041. In particular, the second path D 2042 will be slightly shorter than the first path D 2041 depending upon the level of the stratified flow.

This variation in path length is used by the invention to establish the presence of stratified flow. A more complicated analysis allows the calculation of the level of the stratified flow. Either way, because these level variations are often slight, it is preferable to utilize a measurement very sensitive to these changes in path length. Once the measurements indicate that stratified flow is present, the level, area, flow amount, etc., of the stratified flow can be found.

It has been found that the level of the stratified flow should result in a significant effect on a speed of sound measurement along chord D. Unlike the typical level detector of the prior art, in a gas pipeline the pressure, temperature, and gas composition are variable. This complicates the determination of whether there exists liquid in the bottom of the conduit being measured. This variation in pressure, temperature, and gas composition also makes the speed of sound generally unknown. Thus, if speed of sound is the parameter used to determine the presence of level of liquid in a pipeline, as it is in the preferred embodiment of the present invention, the speed of sound through the flowing gas should be normally be measured independently and near simultaneously with the detection of level in the pipeline. Such contemporaneous measurement of the speed of sound should be made close enough in time to the first that there can be a high level of assurance that variables, such as temperature, pressure, and composition, have not changed enough to signficantly affect the measurement of stratified flow. Where the speed of sound is being measured by an ultrasonic meter, this measurement is made in addition to measuring the velocity of the gas flow along the chords of the ultrasonic meter (such as an ultrasonic meter having chords 2010, 2020, 2030). As an additional advantage to the invention, speed of sound is a measurement that is already made by ultrasonic meters, and thus for the preferred embodiment, minimal changes are required to existing meters.

When there is no liquid in the bottom of the pipeline, the speed of sound measured along path D will be the same as the speed of sound measured from the other chords in the ultrasonic meter. With liquid in the bottom of the pipe, however, the reflection is from the liquid surface (not the bottom of the pipe) and path D is shorter. This makes the transit time shorter and the calculated speed of sound (using the wrong path length) is higher. The difference between the speed of sound measured by chords A, B, and C and the speed of sound measured by chord D can be used to establish the level of stratified flow in pipeline 2000.

Figure 6:
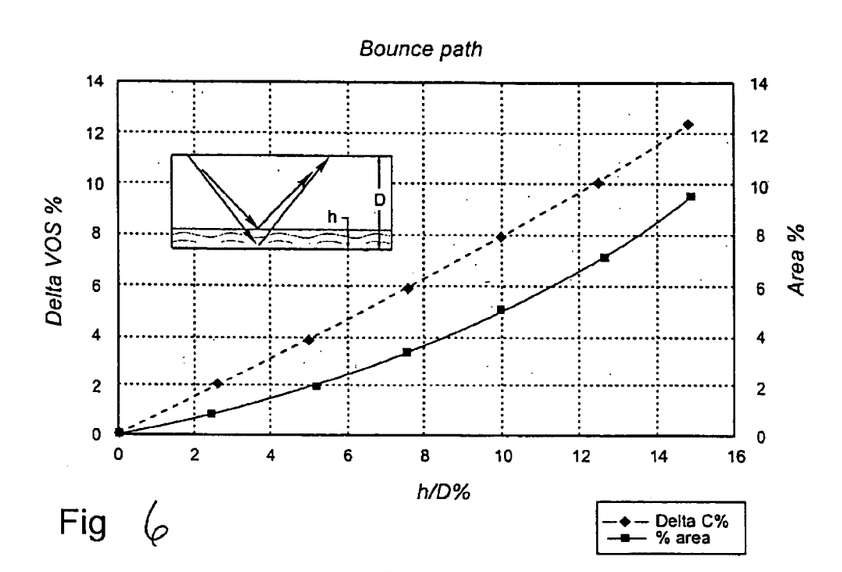
FIG. 6 is a graph illustrating changes in speed of sound versus changes in stratified flow depth.

Referring to FIG. 6, calculations show the effect of h/D (with h=depth of stratified flow and D=pipe diameter) on the change in speed of sound (Delta VOS) and the area occupied by the liquid as a percent of the total pipe area. The sensitivity of speed of sound to changes in the area occupied by the stratified flow can be seen in FIG. 7. As can be seen, a 5% change in area is accompanied by an 8% change in the speed of sound, giving a very sensitive measurement.

As will now be apparent to one of ordinary skill in the art, there is no requirement that a four-chord ultrasonic meter be used with these principles to determine the level of stratified flow in the pipeline. A two-chord level detector as shown in FIG. 8 could also be employed.

Figure 8:
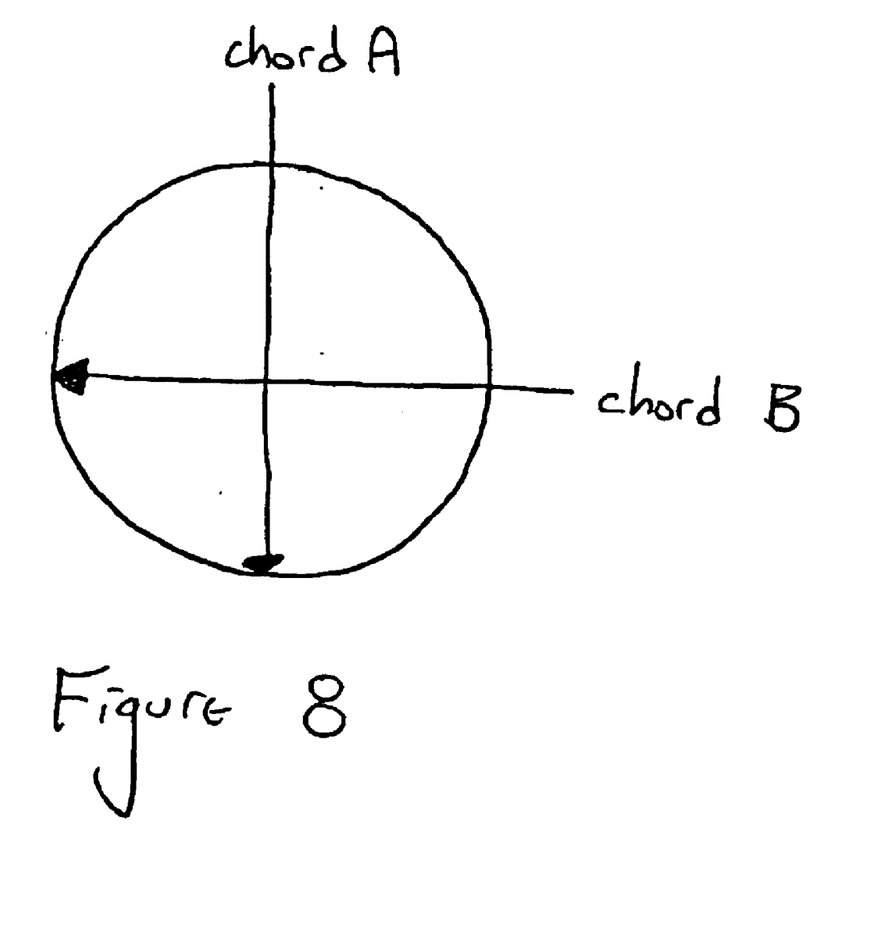
FIG. 8 is an end view of a two-chord ultrasonic meter.

FIG. 8 illustrates an end view of a spoolpiece with chord A and chord B. Ideally, these two chords are vertical and horizontal. Therefore, chord A will loosely be referred to as a vertical chord, while chord B will loosely be referred to as a horizontal chord. Chord B includes two transducers, an upstream transducer and a downstream transducer. Chord A includes two transducers, similar to that shown in FIGS. 4 and 5. As explained above, a difference in upstream and downstream travel times for each of these chords provides (among other things) a velocity of sound (VOS) measurement for any fluid the chord is travelling through.

Figure 7:
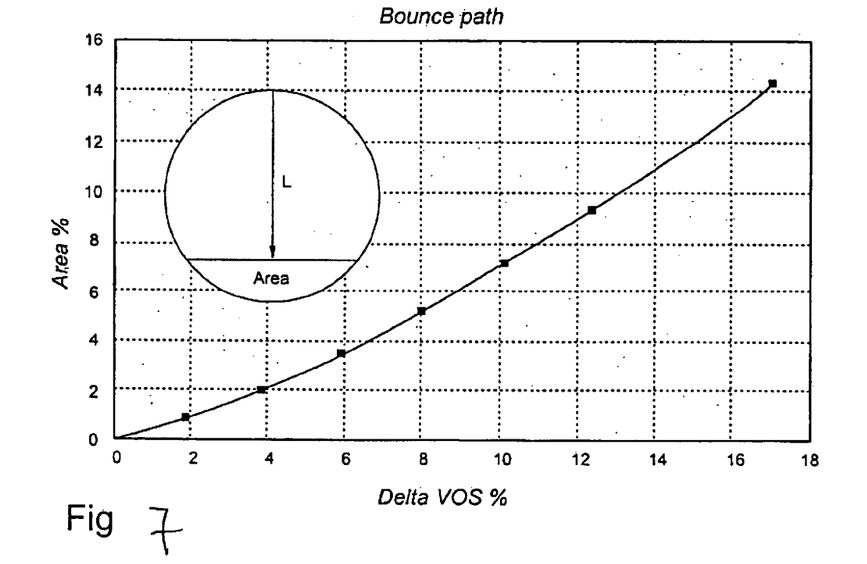
FIG. 7 is a graph illustrating changes in speed of sound versus changes in area for the stratified flow.

With no appreciable liquid on the bottom of the pipeline, the velocity of sound measured on the horizontal and vertical chords is the same. With liquid in the bottom of the pipe, the ultrasonic pulse is reflected from the liquid surface and not the pipe wall. This creates a shorter path length and a shorted transit time is measured. Because any computer or processor associated with the meter bases its VOS calculations on an assumed path length, this results in a higher measured velocity of sound. The difference in VOS between the vertical and horizontal chord, is related by geometry to the liquid level and area occupied by the liquid, as shown in FIGS. 6 and 7.

The speed of the stratified flow can be calculated according to the square root of the ratio of the densities of the flows (i.e. gaseous and stratified) times the speed of the gas. This relationship can be derived because in equilibrium the shear stress of the liquid on the bottom of the pipe is the same as the shear stress of the gas on the liquid. In other words, equilibrium is achieved when the friction at the surface of the stratified flow is the same as the friction at the bottom of the pipe. Consequently, $$\rho_L V_L^2 = \rho_G [V_G - V_L]^2 \qquad (9)$$

Where,
$\rho_L$=density of the liquid
$\rho_G$=density of the gas
$V_L$=velocity of liquid
$V_G$=velocity of gas
This means that, $$V_L = \frac{V_G}{1 + \sqrt{\frac{\rho_L}{\rho_G}}} \qquad (10)$$

Figure 9:
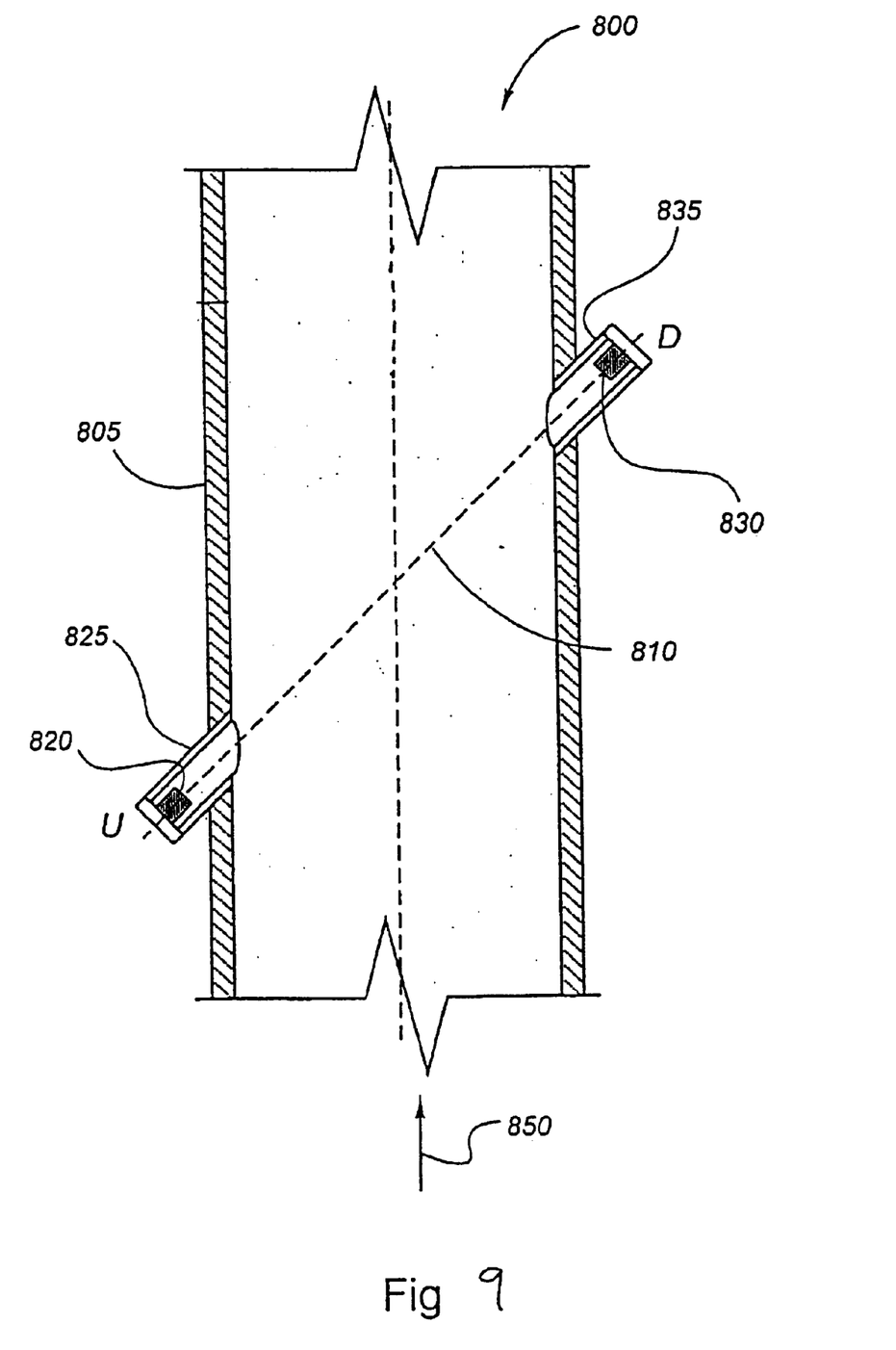
FIG. 9 is a top view of a horizontal chord.

FIG. 9 is a top view of a horizontal chord. Ultrasonic meter 800 includes upstream transducer 825 and downstream transducer 835, each attached to spoolpiece 805. Piezoelectric element 820 houses within transducer 825 while piezoelectric element 830 houses within transducer 835. Transducers 825, 835 also define chord 810. Fluid flows through transducer 800 in direction 850.

Upon understanding of the teachings above, a processor or computer may be programmed to detect the presence of liquid in the pipeline by a statistically significant discrepancy between the measured speeds of sound. The processor or computer may be programmed to estimate accurately the level of liquid in the pipeline. The processor or computer may also be programmed to determine not only the level of liquid in the pipeline, but also the speed of the flow. Such processors may be part of an ultrasonic meter or may be separate. For example, this processor may be the same microprocessor that operates on measured data from an ultrasonic meter.

While preferred embodiments of this invention have been shown and described, modifications thereof can be made by one skilled in the art without departing from the spirit or teaching of this invention. The embodiments described herein are exemplary only and are not limiting. Many variations and modifications of the system and apparatus are possible and are within the scope of the invention. Accordingly, the scope of protection is not limited to the embodiments described herein, but is only limited by the claims that follow, the scope of which shall include all equivalents of the subject matter of the claims.

What is claimed is:

1. A method to determine the amount of stratified flow through a conduit, comprising:
   (a) transmitting through a first portion of said conduit a first ultrasonic signal in a generally horizontal direction from a first upstream location;
   (b) receiving said first ultrasonic signal at a location downstream of said first upstream location;
   (c) transmitting through said first portion a second ultrasonic signal in a generally horizontal direction from a first downstream location;
   (d) receiving said second ultrasonic signal at a location upstream of said first downstream location;
   (e) transmitting through said first portion of said conduit a third ultrasonic signal from a second upstream location, said third ultrasonic signal reflecting off a surface of said stratified flow;
   (f) receiving said third ultrasonic signal at a location downstream of said second upstream location;
   (g) transmitting through said first portion a fourth ultrasonic signal from a second downstream location, said fourth ultrasonic signal reflecting off said surface of said stratified flow;
   (h) receiving said fourth ultrasonic signal at a location upstream of said second downstream location; and
   (i) computing the amount of said stratified flow in said conduit based on the travel times of said first, second, third, and fourth ultrasonic signals.

2. The method of claim 1, wherein said first portion is not said stratified flow.

3. The method of claim 1, wherein said first portion is a gas.

4. The method of claim 1, wherein said first and second ultrasonic signals are used to measure a speed of sound for a portion of said conduit not carrying said stratified flow.

5. The method of claim 1, wherein said third and fourth ultrasonic signals travel in generally vertical directions.

6. The method of claim 5, wherein said first and second ultrasonic signals are used to measure a speed of sound for a portion of said conduit not carrying said stratified flow and said third and fourth ultrasonic signals are used to measure a second speed of sound corresponding to a level of said stratified flow in said conduit.

7. The method of claim 1, wherein said first ultrasonic signal is transmitted by a first transducer and received by a second transducer, said second ultrasonic signal is transmitted by said second transducer and received by said first transducer, said third ultrasonic signal is transmitted by a third transducer and received by a fourth transducer, and said fourth ultrasonic signal is transmitted by said fourth transducer and received by said third transducer.

8. The method of claim 1, wherein said step of computing includes calculating a first measured speed of sound from said first and second ultrasonic signals, and a second measured speed of sound based on said third and fourth ultrasonic signals, the discrepancy between said first and second measured speeds of sound indicating the level of said stratified flow.

9. The method of claim 1, wherein said step of computing said amount of said stratified flow includes calculating the level of said stratified flow in said conduit.

10. The method of claim 1, wherein said step of computing said amount of stratified flow includes determination of the amount of said stratified flow by computing a speed for said stratified flow.

11. The method of claim 10, wherein said speed for said stratified flow is computed from the equation:

$$V_L = \frac{V_G}{1 + \sqrt{\frac{\rho_L}{\rho_G}}}$$

$\rho_L$=density of the liquid
$\rho_G$=density of the gas
$V_L$=velocity of liquid
$V_G$=velocity of gas.

12. The method of claim 1, wherein said amount is the depth of said stratified liquid flow.

13. A method to determine the amount of stratified flow through a conduit, said method being performed by a two-chord ultrasonic meter, comprising:
   (a) transmitting through a first portion of said conduit a first ultrasonic signal from a first unstream location;
   (b) receiving said first ultrasonic signal at a location downstream of said first upstream location;
   (c) transmitting through said first portion a second ultrasonic signal from a first downstream location;
   (d) receiving said second ultrasonic signal at a location upstream of said first downstream location;
   (e) transmitting through said first portion of said conduit a third ultrasonic signal from a second upstream location, said third ultrasonic signal reflecting of a surface of said stratified flow;
   (f) receiving said third ultrasonic signal at a location downstream of said second upstream location;
   (g) transmitting through said first portion a fourth ultrasonic signal from a second downstream location, said fourth ultrasonic signal reflecting of said surface of said stratified flow;
   (h) receiving said fourth ultrasonic signal at a location upstream of said second downstream location;
   (i) computing the amount of said stratified flow in said conduit based on the travel times of said first, second, third, and fourth ultrasonic signals.

14. The method of claim 13, wherein said first and second ultrasonic signals are used to measure a speed of sound for a portion of said conduit not carrying said stratified flow.

15. The method of clam 13, wherein said first and second ultrasonic signals are used to measure a speed of sound for a portion of said conduit not carrying said stratified flow and said third and fourth ultrasonic signals are used to measure a second speed of sound corresponding to a level of said stratified flow in said conduit.

16. The method of claim 13, wherein said first ultrasonic signal is transmitted by a first transducer and received by a second transducer, said second ultrasonic signal is transmitted by said second transducer and received by said first transducer, said third ultrasonic signal is transmitted by a third transducer and received, by a fourth transducer, and said fourth ultrasonic signal is transmitted by said fourth transducer and received by said third transducer.

17. The method of claim 13, wherein said step of computing includes calculating a first measured speed of sound from said first and second ultrasonic signals, and a second measured speed of sound based on said third and fourth ultrasonic signals, the discrepancy between said first and second measured speeds of sound indicating the level of said stratified flow.

18. The method of claim 13, wherein said step of computing said amount of said stratified flow includes calculating the level of said stratified flow in said conduit.

19. The method of claim 13, wherein said step of computing said amount of stratified flow includes determination of the amount of said stratified flow by computing a speed for said stratified flow.

20. The method of claim 19, wherein said speed for said stratified flow is computed from the equation:

$$V_L = \frac{V_G}{1 + \sqrt{\frac{\rho_L}{\rho_G}}}$$

$\rho_L$=density of the liquid
$\rho_G$=density of the gas
$V_L$=velocity of liquid
$V_G$=velocity of gas.

21. A method to determine the amount of stratified flow through a conduit, comprising:
   (a) transmitting through a first portion of said conduit a first ultrasonic signal from a first upstream location;
   (b) receiving said first ultrasonic signal at a location downstream of said first upstream location;
   (c) transmitting through said first portion a second ultrasonic signal from a first downstream location;
   (d) receiving said second ultrasonic signal at a location upstream of said first downstream location;
   (e) transmitting through said first portion of said conduit a third ultrasonic signal from a second upstream location, said third ultrasonic signal reflecting of a surface of said stratified flow;
   (f) receiving said third ultrasonic signal at a location downstream of said second upstream location;
   (g) transmitting through said first portion a fourth ultrasonic signal from a second downstream location, said fourth ultrasonic signal reflecting of said surface of said stratified flow;
   (h) receiving said fourth ultrasonic signal at a location upstream of said second downstream location;
   (i) computing the amount of said stratified flow in said conduit based on the travel times of said first, second, third, and fourth ultrasonic signals, wherein said step of computing includes computing the quantity of stratified flow through the conduit by multiplying a velocity for said stratified flow by a cross-sectional area of said stratified flow.

22. The method of claim 21, wherein said first and second ultrasonic signals are used to measure a speed of sound for a portion of said conduit not carrying said stratified flow.

23. The method of claim 21, wherein said first and second ultrasonic signals are used to measure a speed of sound for a portion of said conduit not carrying said stratified flow and said third and fourth ultrasonic signals are used to measure a second speed of sound corresponding to a level of said stratified flow in said conduit.

24. The method of claim 21, wherein said first ultrasonic signal is transmitted by a first transducer and received by a second transducer, said second ultrasonic signal is transmitted by said second transducer and received by said first transducer, said third ultrasonic signal is transmitted by a third transducer and received by a fourth transducer, and said fourth ultrasonic signal is transmitted by said fourth transducer and received by said third transducer.

25. The method of claim 21, wherein said step of computing includes calculating a first measured speed of sound from said first and second ultrasonic signals, and a second measured speed of sound based on said third and fourth ultrasonic signals, the discrepancy between said first and second measured speeds of sound indicating the level of said stratified flow.

* * * * *